US010092609B2

(12) United States Patent
Wieser et al.

(10) Patent No.: US 10,092,609 B2
(45) Date of Patent: Oct. 9, 2018

(54) PROCESS FOR PREPARING MEDICINAL MYCOLOGICAL PREPARATIONS

(71) Applicants: James A. Wieser, Golden, CO (US); James Martin Bell, Flagstaff, AZ (US); Richard L. Sarnat, Fairfield, IA (US)

(72) Inventors: James A. Wieser, Golden, CO (US); James Martin Bell, Flagstaff, AZ (US); Richard L. Sarnat, Fairfield, IA (US)

( * ) Notice: Subject to any disclaimer, the term of this patent is extended or adjusted under 35 U.S.C. 154(b) by 132 days.

(21) Appl. No.: 14/599,373

(22) Filed: Jan. 16, 2015

(65) Prior Publication Data
US 2016/0206670 A1 Jul. 21, 2016

(51) Int. Cl.
*A61K 36/07* (2006.01)

(52) U.S. Cl.
CPC .......... *A61K 36/07* (2013.01); *A61K 2236/00* (2013.01)

(58) Field of Classification Search
CPC combination set(s) only.
See application file for complete search history.

(56) References Cited

U.S. PATENT DOCUMENTS

| | | | |
|---|---|---|---|
| 4,211,844 A | 7/1980 | Wu | |
| 5,077,201 A | 12/1991 | Eyal et al. | |
| 5,114,734 A | 5/1992 | Kibler et al. | |
| 5,744,187 A | 4/1998 | Gaynor | |
| 5,780,097 A | 7/1998 | Tanaka | |
| 5,804,174 A | 9/1998 | Ishibashi et al. | |
| 5,934,012 A | 8/1999 | Holtz et al. | |
| 6,123,947 A | 9/2000 | Zhou et al. | |
| 6,174,514 B1 | 1/2001 | Cherukuri et al. | |
| 6,261,588 B1 | 7/2001 | Sanaka | |
| 6,299,925 B1 | 10/2001 | Xiong et al. | |
| 6,395,280 B1 | 5/2002 | Yamakoshi et al. | |
| 6,440,448 B1 | 8/2002 | Intelisano | |
| 6,569,475 B2 | 5/2003 | Song et al. | |
| 6,669,972 B2 | 12/2003 | Blortz et al. | |
| 6,726,911 B1 | 4/2004 | Julich et al. | |
| 6,759,049 B2 | 7/2004 | Donatini | |
| 6,783,771 B2 | 8/2004 | Ikekawa et al. | |
| 6,841,180 B2 | 1/2005 | Kim et al. | |
| 6,869,621 B2 | 3/2005 | Hwang et al. | |
| 7,179,488 B2 | 2/2007 | Sherwood et al. | |
| 7,258,862 B2 | 8/2007 | Mahajina et al. | |
| 7,285,279 B2 | 10/2007 | Sun | |
| 7,524,504 B1 | 4/2009 | Bishop et al. | |
| 7,597,910 B2 | 6/2009 | McDowell, Jr. | |
| 7,790,175 B2 | 9/2010 | Eguchi et al. | |
| 7,854,936 B2 | 12/2010 | Bishop et al. | |
| 7,897,154 B2 | 3/2011 | Hiromoto | |
| 7,923,044 B2 | 4/2011 | Bias | |
| 8,097,258 B2 | 1/2012 | Bishop et al. | |
| 8,257,694 B2 | 9/2012 | Daikeler et al. | |
| 8,324,175 B2 | 12/2012 | Ko | |
| 8,357,406 B2 | 1/2013 | Lee | |
| 8,383,127 B2 | 2/2013 | Ales et al. | |
| 8,460,724 B2 | 6/2013 | Chen et al. | |
| 8,481,284 B2 | 7/2013 | Parkin et al. | |
| 8,535,922 B2 | 9/2013 | Nishimoto et al. | |
| 8,753,656 B2 | 6/2014 | Stamets | |
| 8,765,138 B2 | 7/2014 | Stamets | |
| 8,865,888 B2 | 10/2014 | Chen | |
| 9,326,540 B2 * | 5/2016 | Chalupa | A23L 5/32 |
| 2002/0119164 A1 | 8/2002 | Uchiyama et al. | |
| 2003/0161842 A1 | 8/2003 | Wang et al. | |
| 2004/0137012 A1 | 7/2004 | Murata et al. | |
| 2004/0142000 A1 | 7/2004 | Suga et al. | |
| 2005/0002962 A1 | 1/2005 | Pasco et al. | |
| 2005/0008655 A1 | 1/2005 | Uchiyama et al. | |
| 2006/0045887 A1 | 3/2006 | Mahajna | |
| 2006/0057157 A1 | 3/2006 | Mahajna | |
| 2007/0104727 A1 | 5/2007 | Chan | |
| 2007/0244175 A1 * | 10/2007 | Beelman | C07D 233/02 |
| | | | 514/401 |
| 2007/0298049 A1 | 12/2007 | Tominaga | |
| 2008/0019996 A1 | 1/2008 | Mahajna | |
| 2008/0171115 A1 | 7/2008 | Itoh | |
| 2009/0270343 A1 | 10/2009 | Ales | |
| 2010/0003292 A1 | 1/2010 | Gautier | |
| 2010/0330641 A1 | 12/2010 | Nishimoto | |

(Continued)

FOREIGN PATENT DOCUMENTS

| | | | |
|---|---|---|---|
| CN | 102408968 | * | 4/2013 |
| JP | 06078629 | * | 9/1992 |

OTHER PUBLICATIONS

Lu C. et al. Fibrinolytic Enzymes from Medicinal Mushrooms. Biochemistry, Genetics and Molecular Biology Ed. Eshel Faraggi, Chapter 15, 337-362,m Apr. 2012. (Year: 2012).*

(Continued)

*Primary Examiner* — Ralph J Gitomer
(74) *Attorney, Agent, or Firm* — F. Russell Denton, Esq.; Denton Intellectual Property Law Firm, LLC

(57) ABSTRACT

The invention provides medicinal fungal preparations that have twenty or more times more medicinal potency than corresponding medicinal fungal preparations made by prevailing means in the prior art. In particular the invention provides nutrient-supplemented bioactive cell-ruptured cultures of medicinal fungi for which the post-rupture extraction medium is edible or potable, and has no significant side effects. The invention further provides methods to prepare them, and pharmacological preparations based on whole-culture biomass including the growth medium and metabolites.

20 Claims, No Drawings

(56) References Cited

U.S. PATENT DOCUMENTS

| | | | |
|---|---|---|---|
| 2011/0111065 A1 | 5/2011 | Chiang | |
| 2011/0223294 A1 | 9/2011 | Itoh | |
| 2012/0258231 A1 | 10/2012 | Kegasa et al. | |
| 2013/0280376 A1 | 10/2013 | Ulmer et al. | |
| 2013/0302279 A1 | 11/2013 | Simon et al. | |
| 2014/0309414 A1 | 10/2014 | Zhang et al. | |
| 2014/0322260 A1 | 10/2014 | Tani | |
| 2016/0024457 A1* | 1/2016 | Haubrich | C12P 33/00 435/52 |

OTHER PUBLICATIONS

Chen, S. et al. The Effect of Mushroom Beta-Glucans from Solid Culture of Ganoderma lucidum on Inhibition of the Primary Tumor Metastasis. Evidence Based Complimentary and Alternative Medicine vol. 2014, Article ID 252171, 7 pages, Apr. 2014. (Year: 2014).*

Taubert J. et al. A Comparative Study on the Disintegration of Filmentous Fungi. J of Microbiological Methods 42:225-232, 2000. (Year: 2000).*

Yeng A. et al. A Comparative Study of Extraction Techniques for Maximum Recovery of Glutamate Decarboxylase from Aspergillus oryzae NSK. BMC Research Notes 6:526, 2013. (Year: 2013).*

Wong K. et al. Activity of Aqueous Extracts of Lion's Mane Mushroom Hericium erinacreus on the Neural Cell Line NG108-15. International J of Medicinal Mushrooms 9:57-65, 2007. (Year: 2007).*

* cited by examiner

PROCESS FOR PREPARING MEDICINAL MYCOLOGICAL PREPARATIONS

FIELD OF THE INVENTION

The invention pertains to extraction and potentiation methods for pharmaceutically active components from medicinal fungi.

BACKGROUND

Fungi have an illustrious record in drug discovery. The range of active compounds that have been identified include antibiotics, anti-cancer drugs, blood glucose regulators, cholesterol inhibitors, psychotropic drugs, immunosuppressants and even fungicides. Among the important modern fungi-based antibiotics are penicillin, cephalosporins, fusafungine, usnic acid, fusidic acid, fumagillin, brefeldin A, verrucarin A and alamethicin, Fungi are also the source of prominent immunosuppressants, including cyclosporin, mycophenolic acid and mizoribine. Certain statins are derived from fungi, including lovastatin, the pravastatin precursor mevastatin, and the simvastatin precursor monacolin J. And perhaps counterintuitively, fungi are also a source of antifungal drugs such as griseofulvin, echinocandins, strobilurin, azoxystrobin, caspofungin, and micafungin.

Medicinal species are perhaps more common than not among mushrooms. For instance, at least 650 species from 182 genera of hetero- and homo-basidiomycetes have been reported to contain polysaccharides that possess anti-tumor and/or immunostimulative properties; see S. V. Reshetnikov, S. P. Wasser, and K. K. Tan, "Higher Basidiomycetes as a source of antitumour and immunostimulating polysaccharides (Review)," *Int. J. Med. Mushrooms,* 3:361-394 (2001). These polysaccharides appear in fruit bodies, culture mycelia and culture brothers. However generally the fruit bodies are the richest source of the active medicinal principle and contain a greater diversity of bioactive polysaccharides.

Extractions of medicinal mushrooms fall into primarily two categories: hot water methods to isolate polysaccharides and glycoproteins, versus ethanol-based methods to isolate terpenoids, sterols, and other less polar compounds. These separations may be used in complementary ways, for instance to obtain both purified mycogenous carbohydrates and purified terpenoids. In some cases these extractions are accompanied by enzymatic treatments, particularly for breaking down polymeric bulk structures formed from chitin and/or chitosan.

Common examples of hot water extracts used to isolate bioactive carbohydrates and glycoproteins include those from Reishi (*Ganoderma lucidum*), Maitake (*Grifola frondosa*) and Shiitake (*Lentinus edodes*) mushrooms. The Reishi samples typically involve further purification with salts, alkali and dimethylsulfoxide solvent. The Maitake samples typically involve a deproteination step to free the conjugated polysaccharides. Shiitake extracts typically arise from a hot water extract of powdered mycelia, held for 50-60 h at 40-50° C. and allowed to undergo partial hydrolysis by endogenous enzymes, then the residue is extracted with 60° C. water, and the filtrate is freeze-dried to obtain "LEM" product; a different valuable fraction ("LAP") is obtained by using a 1:4 water-in-ethanol solution for the filtrate.

The division between aqueous and solvent-based steps is evident in what Mizuno et al. (1999) have characterized as the typical approach to extract anti-cancer polysaccharides from mushroom fruit-bodies, mycelium and liquid media. First dried material (mushroom powder or mycelium) is repeatedly heated in 80% ethanol to extract and remove low molecular weight substances. The media for serial crude fractionations are water (100° C., 3 h, fraction 1), 1% ammonium oxalate (100° C., 6 h, fraction 11), and finally 5% NaOH (80° C., 6 h, fraction 111). The resulting polysaccharides are then further purified by ethanol, fractional precipitation, use of acetic acid to re-precipitate, ion-exchange chromatography, gel filtration chromatography and affinity chromatography. See T. Mizuno, "The extraction and development of antitumour-active polysaccharides from medicinal mushrooms in Japan," *Int. J. Med. Mushrooms,* 1:9-29 (1999).

Purities by that method can exceed 99%, but a thriftier and much more efficient protocol achieves 87% purity (e.g., for the beta glucan lentinan from *Leninus edodes*) by simply precipitating the carbohydrate in ethanol and freeze-drying in liquid nitrogen, followed by lyophylization (evaporation), extraction with boiling water, and reiterative cycles of centrifuging and redissolving in 95% ethanol. See A.-T. Yap and M.-L. M. Ng, "An improve method for the isolation of lentinan from the edible and medicinal shiitake mushroom, *Lentinus edodes* (Berk.) Sing. (Agaricomycetdeae)" *Int. J. Med. Mushrooms,* 3:6-19 (2001).

Where the compound of interest is an exudate, the methods are even easier: e.g., nearly neat ethanol is used to absorb the compound, then a precipitate is collected by centrifugation, then the precipitate is redissolved in and for two days dialyzed against distilled water, and analysed by gel filtration chromatography (Babitskaya et al., 2000).

Extraction of less polar organics proceeds by other methods. Typically these involve organic solvents, in particular ethyl acetate, methanol or ethanol, though others are also used. See, e.g., I. J. Nieto and C. A. Carolina, "Triterpenoids and fatty acids identified in the edible mushroom *Pleurotus sajor-cajú*," *J. Chil. Chem. Soc.,* 53(2):1515-1517 (2008). An example of recent innovation in this area is the use of electrophoretic methods for inexpensive extraction of triterpenoids from Reishi. See C.-R. Cheng, "Preparative isolation of triterpenoids from *Ganoderma lucidum* by countercurrent chromatography combined with pH-zone refining," *Food Chem.,* 130(4):1010-1016 (2012).

What is common for all of these methods is the objective of enhancing the potency and safety of fungal compounds for medicinal use. The emphasis on purification, isolation and identification has arisen because in most cases formulation designers do not know how to optimize the identities, ratios or concentrations of fungal molecular natural products either during fungiculture or during harvesting and extraction. In fact, often the physiological basis of the medicinal effects in humans is also not well understood. Thus there is an ongoing need for improved extraction methods and improved medicinal formulations of fungal species.

BRIEF SUMMARY OF THE INVENTION

The invention provides medicinal fungal preparations that have twenty or more times more medicinal potency than corresponding medicinal fungal preparations made by prevailing means in the prior art. In particular the invention provides nutrient-supplemented bioactive cell-ruptured cultures of medicinal fungi for which the post-rupture extraction medium is edible or potable, and has no significant side effects. The invention further provides methods to prepare them, and pharmacological preparations based on whole-culture biomass including the growth medium and metabolites.

In one embodiment the invention is a process for preparing high-potency fungal medicinal materials comprising the steps of:
a) growing organisms from a medicinal fungal species in a culture on a cell-based growth medium, wherein:
   i) the fungal species is a species that is edible when raw; and
   ii) the cell-based growth medium is edible;
b) placing at least a portion from the fungal organisms and at least a portion from the cell-based growth medium into an extraction medium;
c) in the extraction medium, rupturing substantially all cells of the fungal organisms and the growth medium cells that had been placed therein, thereby forming a post-rupture bioactive extraction medium; and
d) providing the post-rupture extraction medium in bioactive form as a medicinal composition.

In another embodiment the invention is a pharmaceutical composition comprising:
a) an extraction medium;
b) a first extract, wherein:
   i) the first extract is derived from one or more organisms from at least one medicinal fungal species;
   ii) the fungal species in the extract is or are edible when raw; and
   iii) the first extract is prepared by a step of rupturing substantially all of the cells in the one or more medicinal fungal organisms, wherein:
      A) the rupturing step is performed in the extraction medium;
      B) the extraction medium has a temperature that is no less than 0° C. nor more than 40° C. during the rupturing step; and
      C) the extraction medium has a pH that is selected from the range of 4 to 10, inclusive;
c) a second extract, wherein:
   i) the second extract is derived from an edible cell-based growth medium;
   ii) the medicinal fungal organisms had been grown on the growth medium from which the second extract is derived; and
   iii) the second extract is prepared by a step of rupturing substantially all of the cells in the cell-based growth medium, in the same step as for the rupturing of the medicinal fungal organisms;
wherein the combination of the extraction medium, first extract and second extract is in bioactive form.

In a further embodiment the invention is a method of treating a subject in need thereof, comprising providing a medicinal composition wherein:
a) the medicinal composition comprises an extraction medium, a first extract and a second extract;
b) the extraction medium is selected from the group of aqueous solutions consisting of: those containing an edible oil; those containing ethanol; and those containing neither edible oil nor ethanol;
c) the first extract comprises fungal cellular material from one or more medicinal fungal organisms, wherein;
   i) the one or more medicinal fungal organisms are selected from species that are edible when raw;
   ii) the fungal cellular material consists of residue from cells that have been ruptured in the extraction medium; and
d) the second extract comprises substrate cellular material from a cell-based growth medium, wherein;
   i) the cell-based growth medium is intimately associated with the fungal cellular material as a substrate upon which the medicinal fungal organisms grew prior to being ruptured;
   ii) the substrate cellular material consists of ruptured cells; and
   iii) the first and second extract are well mixed in the extraction medium;
wherein the combination of the extraction medium, first extract and second extract is in bioactive form.

DETAILED DESCRIPTION OF THE INVENTION

The invention may be further understood by consideration of the following definitions.

The term "fungal" means pertaining to or derived from a fungus. The term "fungus" as used herein has its usual and ordinary meaning in the field of mycology at the time of this filing. The term "macrofungus" refers to a member of a fungal species for which the fruit bodies are visible to the human eye without magnification. The term "microfungus" refers to a member of a multi-cellular fungal species for which the fruit bodies are not visible to the human eye without magnification. The term "yeast" refers to a member of a single-cellular fungal species, and includes but is not limited to species that are widely known in the bakery arts, brewing arts and medical pathology. The invention as described herein encompasses use for macrofungi, microfungi and yeasts, to the extent the same are medicinal and are edible without cooking.

The term "medicinal material" means a substance that has medicinal properties for human or animal use.

The term "medicinal composition" means a composition comprising a medicinal material.

The term "high-potency" as used with respect to fungus-derived medicinal compositions according to the invention means that they have an efficacy that is at least ten times that of the same mass of dry fungal preparations from the same species, where the mass of each is determined as a function of their dry weight.

The term "rupture" as used herein with respect to a fungal cell or plant cell means to cause the cell to suffer physical damage in a manner that allows the direct exchange of material between the inside and outside of the cell. Examples of rupturing may include but are not limited to tearing, shearing, splitting, puncturing, crushing, delaminating and the like. In a particularly preferred embodiment the rupture may be accomplished by use of a high speed blade. However the invention is not so limited and rupturing may be accomplished by means such as milling, atmospheric pressure, osmotic pressure, and other means for low temperature rupturing that will not denature enzymes.

The term "ruptured together" as used with respect to fungal and growth medium cells means that both fungal cells and cells from a substrate on which the fungal cells grow are present in the same medium and are both ruptured in that medium.

The term "in ruptured form" as used herein with respect to a cell means that it has been ruptured.

The term "contents" as used with respect to ruptured cells means their contents, whether in the form of organelles, tissues, cytoplasm, structural polymers, enzymes and other proteins, small molecules, or another form, and whether they are intact as before the rupturing or altered by the rupturing or post-rupture modification. The term "contents" is not limited by the nature of their physical state, whether liquid, solid, gaseous, some combination of those, or some other physical state.

The term "bioactive", as used herein with respect to ruptured fungal cells and their contents, means that the media in which the post-rupture cells and their contents are located continues to manifest biochemical activity and pharmacological effects with effects that are comparable to, and at levels that are comparable to, those of the fresh fungal material before rupturing. In this context, by comparable is meant: that the biochemical properties are much more like those of live intact fungi of the same species than like those of desiccated intact fungi of the same species that have been mechanically comminuted in water in a manner like that of the ruptured cells. Typically in the bioactive medium the proteins and enzymes remain largely undenatured, and the ruptured cells have not been heated to a temperature that would kill intact cells. By "in bioactive form", as used herein with respect to extraction medium is meant that it retains at least 30% of its bioactivity that existed immediately after the cells were ruptured there.

The term "substantially all" as used with respect to rupturing of cells means the proportion represented by any unruptured cells is negligible. In particular embodiments the term substantially all means at least 90%, at least 95% or at least 99%.

The term "substantially all" as used with respect to providing contents of ruptured cells in a medicinal composition means that following rupturing of the cells the medium is not purified except optionally by removing solids such as by filtering or centrifugation.

The term "culture" as used with respect to growth of fungi means the growth medium including the fungal cells contained there, and when used as a verb means the act of cultivating fungal cells in such a medium.

The term "portion" as used with respect to a culture of fungi for which some cells are ruptured at a particular point in time refers, refers to that portion of the culture which is removed for purposes of that treatment by rupturing.

The terms "protein," "peptide" and "enzyme" have their usual and ordinary meaning in biochemistry.

The term "denatured" has its usual and ordinary meaning in biochemistry, and refers to a state of having been treated under conditions that are sufficient to cause unfolding of a polymer that is present such as an enzyme, other protein, or duplex nucleic acid such as DNA. Non limiting illustrative denaturing conditions include heat, introduction of a surfactant such as sodium dodecylsulfate (SDS), and the like.

The term "undenatured" refers to biochemical species that are capable of being denatured under some conditions, but that are not denatured and thus retain their respective bioactive conformations.

The term "denaturing compound" means a compound such as sodium dodecylsulfate (SDS) that interacts with proteins to cause them to rearrange and/or dissolve, thereby losing their bioactive conformation.

The term "intact cells" as used with respect to the invention means cells that have not been ruptured.

The term "cell-based growth medium" means a medium that contains plants and/or plant cells to serve as substrates suitable to serve as a nutritional source for fungal organisms that are desired to grow in the medium. The medium may optionally in addition contain one or more minerals, vitamins, organic additives, and/or other nutritional content.

The term "mixer" means a mechanical mixer that is capable of operating at blade speeds that can cause the rupturing of fungal cells and/or plant cells in solution.

The term "mixer blade" means the mixing blade of a mixer.

The terms "extract" and "extraction" as used with respect to the invention refer to protocols that cause the release of internal substances from a cell, such as by mechanical force, maceration by solvents, and/or other methods.

The term "extraction medium" as used with respect to the invention means a medium in a physical state that is an ordinary liquid, a supercritical fluid, or some other physical state, in which fungal cells are ruptured or otherwise treated. Examples of a liquid that may serve as an extraction medium include water, ethanol, aqueous ethanol, fruit juices, dairy milk, vegetable juices, soy milk, and the like. The term "milk" as used herein with respect to fungal cells and/or their contents in a solution means the solution—with or without solid or gaseous constituents—that results after rupturing of fungal cells is performed in the extraction medium.

The term "solution" means a fluid, regardless of whether it is homogeneous, contains solids, or has solutes dissolved in it.

The term "suspension" means a solution that comprises undissolved solids that remain suspended but have not precipitated out or floated to the top of the solution.

The term "edible oil" means a food-grade oil or other pharmaceutically acceptable oil for ingestion by humans.

The terms "temperature" and "pH" have their usual and ordinary meaning in the fields of chemistry and biochemistry.

The term "temperature that would kill intact cells" means a temperature at which cells in a liquid or other fluid medium would be unable to survive for the period of time for which the temperature is applied. Cells vary somewhat in their ability to withstand heat. In one illustrative embodiment the temperature is at least 40° C. In one illustrative embodiment the temperature is at least 45° C. In yet another illustrative embodiment the temperature is at least 50° C.

The term "generated" as used with respect to compounds produced by a cell means that they are biosynthesized by that cell.

The term "high-pressure treatment" means a treatment such as pascalization or supercritical fluid carbon dioxide in which a culture of fungi is exposed to a pressure that is greater than 50% more than atmospheric pressure. For some embodiments the pressure is in the range of 7 MPa or more (≥70 atm); for others it is in the range of 300 MPa or more.

The term "biomass" as used with respect to fungal species means the solids that are present. For unruptured cells it includes the entire mass of the fungal species. For ruptured cells it refers to the residual solids. And for fungal cells that have been ruptured together with substrate cells for a culture it refers to the collective solids.

The term "subject" as used with respect to a medical condition means a human or other animal in need of preventive measures or a therapeutic treatment for that condition.

The term "affliction" means a medical condition such as a pathologically caused disease, autoimmune disorder, wound or other acute or chronic medical condition.

The term "neurological disorder" has its usual and ordinary meaning in the fields of neurology and neuropsychology. Nonlimiting illustrative recognized symptoms include paralysis, muscle weakness, poor coordination, loss of sensation, seizures, confusion, pain and altered levels of consciousness. Nonlimiting examples of disorders include: brain damage such as at the frontal, parietal, temporal or occipital lobe; brain dysfunction such as for aphasia, dysgraphia, dysarthria, apraxia, agnosia, or amnesia; spinal cord disorders; peripheral neuropathy and other peripheral nervous system disorders; cranial nerve disorder such as trigeminal neuralgia; autonomic nervous system disorders such as dysautonomia or multiple system atrophy; seizure disorders such as epilepsy; movement disorders such as Parkinson's disease, essential tremor, amyotrophic lateral sclerosis, Tourette's Syndrome, Multiple Sclerosis; sleep disorders such as narcolepsy; headache such as migraines, cluster headache and tension headache; lower back and neck pain; central neuropathy; and neuropsychiatric disorders such as attention deficit hyperactivity disorder, autism, some cases of obsessive compulsive disorder, Huntington's disease, Alzheimer's disease and organic psychoses.

The terms "cancer" and "metastatic" have their usual and ordinary meaning in the field of medical science.

The terms "Parkinson's Disease", "Fahr's Disease" and "Multiple Schlerosis" have their usual and ordinary meaning in the field of medical science.

The terms "Post-Traumatic Stress Disorder", "depression", "bipolar" and "sleep disorder" have their usual and ordinary meanings in the field of psychology.

Discovery that Prior Art Methods Sacrifice Most of the Fungal Medicinal Potency.

Functional foods and supplements have provided increasing fuller complements of bioactive compounds from fungal extracts. Most of these contain extracts of interest, usually from only the fruiting body (i.e., the mushroom) but in some cases from the mycelium or both. However some leading U.S.-based providers of medicinal mushroom biomass also include in their supplements metabolites and bio-transformed grain from the fungal growth culture. In any case the typical post-harvest process involves drying the biomass or fermented grain culture, then pulverizing and blending it for further processing and extraction or for use as whole, dry mixtures. In some cases the drying process also includes pasteurization or other heat sterilization.

The inventors have discovered that, surprisingly, the methods in current widespread use to harvest and process medicinal fungi result in as much as 99% loss of their pharmacological activity relative to the pharmacological activity as grown. From this it appears that it is desirable to avoid denaturation of proteins and enzymes, and to avoid or minimize the usual effects of cell death and cytoplasmic degradation. It appears that in part fungal cell signaling functions during and after harvesting play an important role in production of therapeutic fungal natural products, though the invention is not so limited. Thus harvesting and post-harvest processing require methods that keep the bioactivity, though not necessarily with the cells intact.

Discovery of Benefits of Retaining Bioactive Cultures in a Ruptured State.

Medicinal formulations are commonly prepared by extraction of the biomaterial with hot water, e.g., to release medicinal high molecular weight complex carbohydrates, or by treatment with a low molecular weight alcohol such as ethanol to release smaller molecules. In this they are comparable to plant genera that are extracted by conventional means—soxhlet extraction (3-18 hours at reflux temperatures), sonification (1 hour, optionally with heat) or maceration (3-4 days)—or more advanced methods in which the extraction is aided by a supercritical fluid (carbon dioxide, 30-100 minutes, 40-100° C., 250-450 atmospheres), microwaves (80-150° C., 10-40 minutes, optionally pressurized by the heating if the vessel is sealed) or a pressurized liquid (80-200° C., 20-40 minutes, 10-20 bar. Any of these are usually done in the presence of methanol or ethanol, optionally. Those methods rely on heat that may lead to denaturation, and in any case tend to separate out compounds.

In addition the inventors have found that it is beneficial to retain the bioactive compounds in the same medium from which they are released from the cell. In particular the invention harvests and processes the entire biomass of a pure culture of fungi, e.g., including the grain upon which a mushroom is growing because the fungus secretes useful natural products onto that medium, and because fermentation products of the grain support the ongoing biochemical activity of the cell contents. Similarly, processing the entire biomass preserves and enhances the content of primary and secondary metabolites and of medicinal fermentation products. Some or all of these may have a signaling function for cells. By retaining the biochemical system as a living whole, regardless of disruptions to cell walls or membranes, a fuller complement of molecular natural products is produced and collected, and non-obvious synergies have been realized.

Consequently the present invention employs treatment protocols that rupture cultured fungal cell walls at harvest to release medicinal contents, but the treatment minimizes denaturing conditions and preserves the cytoplasm in live form to the extent feasible even after rupturing of cell walls. Thus the enzymes and their complexes, primary and secondary metabolites, ATP and cofactor content, medicinal compounds, fungal cell signaling compounds, and fermented grain growth medium are maintained together under "live" conditions in a "wet" mix with minimal heat. The contents can then be pressurized, which among other benefits can lower the activation energies for enzymatic reactions. Low-temperature pasteurization could also be done as an antimicrobial step. This combination of steps is much more economical than prevailing methods that isolate compounds and then recombine them.

Benefits of Retaining Bioactive Cultures During Extraction.

Currently the prior art kills the mycelium of fungal cultures at the time of harvest to release their contents because the human digestive system cannot break down the fungal cell walls, which are made of chitin. The inventors leave the mycelium alive to the extent feasible during aqueous extraction and during lipophilic extraction. It has been found that the cells survive for three days or more and that the extracts have 20-fold to 100-fold more medicinal potency than traditional extracts of the same mushroom species. I.e., samples of commercially available extracts of the same species have potencies in the range of 1% to 5% of that observed for the present invention. When stored in liquid form at room temperature without additives extracts of the invention retain maximum potency for about three days. When refrigerated they retain maximum potency for four days after the cells are ruptured; then beginning on the fifth day they lose about 30% potency per day until they have no potency by the eighth day. This same phenomena has been observed across all fungal species that the inventors have investigated for use with the invention.

Based on tests of the extracts, the inventors have identified unprecedented activity, including nerve regeneration factors as well as anticancer factors. The inventors have further assessed safety in investigations involving clinically relevant doses for 100 subjects over about 18 months: no major or minor deleterious clinical side effects were reported by those test subjects, such as allergic reactions, gastrointestinal intolerance, headaches, rashes, myalgias or arthralgias. The only common complaint has been that the emulsion (i.e., the extract mixture) tastes like mushroom soup, which some subjects dislike. That flavor does become slightly stronger with each passing day, even under refrigeration.

Discovery of Benefits of Delivering Bioactive Cultures in the Form of Emulsions.

The inventors have also found that preparations of the invention are more potent when delivered in a form that can survive passage through the stomach without excessive decomposition. In particular preparations containing edible oils have proved to be useful for this purpose, and oil-in-water emulsions are particularly useful although the invention is not so limited.

The fungal species for which the invention is particularly useful include any that are both (1) edible without being cooked and (2) have medicinal properties. Many fungal species contain toxins that prevent safe eating unless—in many cases—they are cooked. Because the present invention delivers essentially "raw" fungal material to users, and does not require heat nor provide other means to detoxify natural products apart from may already exist in the fungus or the substrate and growth media, such species would be inappropriate for use with this invention unless detoxified at some stage. However there is a spectrum of views on what must be cooked. Some observers insist that every species of edible mushroom should be cooked before eating, even if it is cultivated with highly sanitary protocols. For instance common white button mushrooms are universally consumed raw on salads or as finger foods, yet contain natural hydrazines that could be carcinogenic if consumed in pure form or very large amounts. White button mushrooms would be considered edible for purposes of the invention, to the extent that the respective users would eat them in that state.

As to medicinal properties, an objective of this invention is to enhance medicinal potency of "mycomedicines", i.e., those based on fungi. Thus it is important that the species of fungi in cultures according to the invention not only all be edible but include at least one species that possesses medicinal properties. In some embodiments a single culture might have two or more medicinal species, provided that their effects do not result in significantly undesirable cross-reactions in the body.

Clinical Summary:

The subjects who were enrolled in the clinical trials were willing adults who met any of the following criteria: (a) affliction with a neurological degenerative state; (b) affliction with an already documented late-stage cancer; or (c) interest in experiencing reported enhanced but non-psychedelic subtle sensory perceptions attributed to use of the extracts. Positive results were identified on a case by case basis, based on self-reports or qualitative clinical observation of increased return to function of a previously debilitated activity (such as a return of speech, ambulation, increased energy and mental clarity). For cancer patients more exact and objective findings were also included such as from serial CAT scans, blood work, etc.

The administered fungal biomass has the properties of a true adaptogen in that its action in subjects is apparently selective against the primary physiological dysfunctions, across a wide range of clinical conditions. The inference of adaptogen-like selectivity was supported by the apparent physiological distribution of benefits within the subjects.

A variety of clinical results are shown below, however the physiological mechanisms that gave rise to these medical results are not completely clear. Without being bound by theory the inventors hypothesize that the erinacine and hericenone compounds in Lion's Mane behave as if they are nerve growth factors. Thus after crossing the blood brain barrier in part with the aid of liposomes delivery vehicles, these compounds putatively then trigger regeneration of at least one critical type of neurotransmitter from the several scores of types that exist. Put another way, it appears that nutrigenomics may serve to achieve neurogenesis. Lion's Mane also appears to be particularly effective as a potentiator of other fungal extracts of the invention but the invention is not so limited. Also, recent reports by others have found that chitosan nanoparticles can serve as delivery vehicles for a small molecule drug, naproxen (in that case for known photodegradation of intercalated DNA), so it is conceivable that small particles of chitosan in medicinal compositions of the invention may function as delivery vehicles here also. See M. Gouda, U. Elayaan and M. M. Youssef, "Synthesis and Biological Activity of Drug Delivery System Based on Chitosan Nanocapsules," *Advances in Nanoparticles,* 3:148-158 (2014).

Exemplary Species:

The utility of the invention method has been confirmed for several non-limiting illustrative known medicinal mushroom species, including for Lion's Mane (*Hericium erinaceus*), Reishi (*Ganoderma lucidum*), Turkey Tail (*Trametes versicolor*), Shiitaki (*Lentinus edodes*), Button/Portobello/Crimini (*Agaricus bisporus*). Royal Sun Agaric (*Agaricus blazei/brasiliensis/ruiotegulis*), Enoki (*Flammulina velutipes/populicola*), Maitake (*Grifola frondosa*) and Oyster Mushrooms (*Pleuroyus ostreatus ipulmonarius*). In general potency is in the range of 20 to 50 times higher than that observed for traditional dry mushroom materials from the same species but can be higher.

Combinations:

The preparations of the current invention exhibit several pharmacodynamic effects that are strikingly different from those of standard fungus-based medicinal compositions. For instance, it is common in the prior art to combine dried material from five to ten fungal species when preparing a medicinal composition. However at the enhanced potencies of preparations of the invention cross reactions become more significant. In our observations of the invention two medicinal mushroom species may often be combined safely, but special caution should be exercised as to health effects when combining more than two species. The exact nature of the undesirable effects is not known, but is assumed to arise from cross-reactions and from the greater potency of extracts of the present invention.

Combinations are particularly useful when there are synergistic effects. As an example, extracts of the invention that include Lion's Mane appear to be synergistic with enhance the efficacy of respective coadministered species such as Reishi, Turkey Tail and Shiitake. Other examples include the tendency of Turkey Tail to enhance mycogenic activity in the bones and the tendency of Shiitake to enhance mycogenic activity in the pineal gland, but again the invention is not so limited.

Extraction of Fresh as Opposed to Dried Materials:

In general the resulting compositions are more healthful when preparations according to the invention are made from fresh fungal material. When extracts and emulsions were made according to the invention beginning with dried fungal materials, the resulting products had more toxic effects at least for some species, thus the maximum reasonable dose was significantly lower and in any case merits extra attention before it can be assumed that dry fungal material will yield results that rival those of fresh fungal material.

It should also be noted that some bioactive compounds tend to be more concentrated in fungal fruit bodies whereas others tend to be more concentrated in mycelia. Thus to achieve desired effects either the fruit bodies or alternatively the mycelia of a species may be selected for separate extraction, or both may be extracted simultaneously. In the present illustrations both components were extracted together but the invention is not so limited.

Other Caveats:

Although most medicinal mushroom species evaluated have produced desirable effects in extracts and emulsions according to the invention, caution should be exercised when evaluating a species for which an extract is used the first time. As an example, Royal Sun Agaric (*Agaricus blazei* Murill; AbM) is an edible, medicinal mushroom used traditionally against cancer and chronic hepatitis, and also as a health food market. Royal Sun has recently been shown to have strong immunomodulating properties. However it is also known that Royal Sun extracts from different sources and manufacturers vary substantially in their medicinal potency. See G. Hetland et al., "Effects of the medicinal mushroom *Agaricus blazei* Murill on immunity, infection and cancer," *Scand. J. Inmmunol.*, 68 (4):363-370 (October 2008). When extracts of Royal Sun were made and used according to the present invention their activity was less stable over a 24-hour period than was that of Lion's Mane, Reishi or Shiitake, and side effects were more marked. Similar effects were observed when using the present invention to make medicinal preparations in which the starting material was a commercially available dried powder of Royal Sun. Thus reasonable prudence should be exercised, and the dosing and benefit should be tailored to the patient, with lower preliminary trial doses where appropriate.

Exemplary Growth Conditions:

Fungi may differ by species as to their preferred growth media and culture conditions. As non-limiting illustrative examples, the Lion's Mane and Reishi were grown separately from inception as mushroom spawn within their respective self-contained sustainable spaces, in order to capture all mycelia, primordial growth and extracellular exudates—e.g., extracellular enzymes—thereby retaining all of the valuable byproducts of natural growth. A further advantage of this approach is that the mycelium predigests the substrate so that nutrients from the substrate are in bioavailable forms when consumed by the end user. The growth medium was certified organic rye grain, together with the naturally occurring minerals dolomite/agricultural lime (calcium magnesium carbonate $CaMg(CO_3)_2$) and gypsum (calcium sulfate dihydrate $CaSO_4.2H_2O$). However other grains or alternatively non-grain substrates may also be used, and alternative mineral and/or organic supplements may be employed, preferably provided that the substrate is edible and non-toxic to humans when the fungal culture is harvested. Examples of alternate grains include wheat, corn, rice, millet, oats, barley, triticale and the like. Examples of non-grain substrates include but are not limited to legumes (e.g., soybeans, red beans, lentils, etc.), tubers (e.g., potatoes, yams, etc.), starchy roots (e.g., carrots, cassava, etc.), and fruits (e.g., apples, bananas, berries, etc.). Examples of other mineral and organic supplements for cultures include but are not limited to salts of Group I and II metals, salts of transition metals, phosphorous compounds, sulfates, sulfites chlorides, phosphates, nitrates and nitrites, vitamins, amino acids, provitamins, and organic metabolites.

For a typical culture medium, 25 pounds of organic rye was placed in a 35-gallon pot which was filled with hot tap water, and the water was then poured off while retaining the grain in place. This step was performed three times to rinse off contaminants and spores, then the grain-filled pot was filled with hot water a fourth time and soaked for 12 to 16 hours. Then the rye was parboiled and the extra water is evaporated as steam by tossing the grain; during tossing the grain was also mixed with a mineral supplement of 100 grams of a 50:50 mixture of gypsum and dolomite. This action completely coats each kernel with the minerals, which further serve as drying and anti-caking agents for the culture medium.

Rye that had been treated in this manner was then provided as a horizontal layer of culture medium about 1.5 inches thick. This differed from the usual practice of using vertical bags of culture medium to save space on shelves. But the horizontal layers provided more convenience in removing only the desired amount of substrate and minimizing exposure of the unused portion.

Collection proceeded as follows. For Reishi, once the primordial stage became visible the product was shipped and refrigerated upon arrival to retard active replication and extend the shelf life.

For Lion's Mane growing on a substrate layer about 1.5 inches thick of the culture medium, fruit bodies form an adjacent layer. When the layer of fruit bodies was itself 1.5 inches thick, the product was shipped and refrigerated upon arrival to retard active replication and extend the shelf life. An advantage to this protocol is that at the time of collection (i.e., shipping, etc.), the mycelium contains the pharmaceutically active ingredients that are eranicines and the fruiting body contains the pharmaceutically active ingredients that are hericenones, thus both types of compounds were conveniently present and conveniently distributed.

Exemplary Processing:

Unlike current commercially available forms of these two product species, which are processed by either dehydration or freeze drying, the invention process employed aimed to create live cytoplasmic extracts by high speed disruption of the live cell membrane. Thus for a particular cultured species a portion of the culture and its growth medium was placed into a high speed blender, suitable devices are well known to persons of ordinary skill in the art and include blenders from, e.g., the respective manufacturers of the WARING®, OSTER®, NINJA® and VITAMIX® brands. In addition to the culture and growth media, filtered water and organic olive oil were placed into the blenders, which were then run at "high speed" setting for about 3 minutes or until any larger grain particles were no longer visible. The ratio of biomass to filtered water was 1:4, and the amount of organic olive oil was one teaspoon per 16 ounces of water; these relative amounts remained the same regardless of whether a particular blender run processed more or less biomass than average.

The resultant emulsion "milk" was then filtered through a small-aperture micro filter, such as extra large coffee filters (paper or metallic), nut-milk bags or cheese cloth, in order to remove any remaining larger particles from the substrate growth medium. The modalities for filtering that are listed here are very diverse in their maximum pass-through particle sizes, for instance a layer of a typical cheesecloth has a 300-micron cut-off and permits passage of readily visible particles, whereas a typical paper coffee filter has a 1-micron cut-off and excludes whole cells and other particles that are well below the 40-micron minimum size that is visible to the eye.

Because the growth medium is both edible and safe, the degree of blending to comminute it or the degree of filtering to remove it is merely a matter of subjective taste. The inventors have found no significant clinical loss when more thoroughly filtered fungal culture "milks" were administered to subjects. But it should not be overlooked that mushroom solids in fact often have a medicinal role themselves. Thus for instance chitins and beta-glucan polysaccarides in a particular molecular weight range (they are polydisperse) are known to promote a Th1 cytotoxic immune response (cell killing) as opposed to a Th2 humoral immune response (pro-inflammatory). The available data in the literature seems to suggest that the balance between the Th1- and Th2-mediated responses plays an important role in immune regulation for a number of diseases including cancer, allergies and asthma. Thus the ability of mycopolymers to modulate the Th1 response in the immune system suggests that it can address inflammation, metabolic activity and with cancer, angiogenesis as well as reduced cytotoxic activity.

The filtrate is essentially a suspension because particles smaller than the filtering cut-off dimensions can pass through. Particularly for emulsions, at least visually in most cases these have appeared to be colloidal dispersions. However the solution heterogeneity was not a detriment, and as noted above can be a benefit. In addition, microparticulate chitin has been reported to act as a delivery vehicles for the natural compounds that serve as the medicinal active species. And, also to the extent that fungal solids remain present in the "milk", any small-molecule pharmacodynamic compounds associated with the solids will be available for ongoing extraction by the human body's own fluids and tissues.

Following filtering, when present, the "milk" was then refrigerated to extend its shelf-life. The product life depends on the particulars of the ingredients, production conditions and storage conditions, but generally the product remained fresh and active for at least three to four days after the rupturing. Pasteurization and freezing are additional options to extend the useful life of these mushroom milks.

Exemplary Follow-on Processing:

For fungal cultures that are processed as above, at three days after extraction the products begin to lose about 30% of their activity per day, presumably due to digestion by live enzymes. In some embodiments according to the invention, the emulsion shelf life is extended by applying high fluid pressure (high pressure processing, HPP) or high pressures of $CO_2$ to the liquefied product. HPP, also known as pascalization, is a cold pasteurization technique by which microorganisms and some enzymes are inactivated. Typically the product is sealed in a vessel, and the HPP applies a high level of isostatic pressure (e.g., 300-600 MPa, or about 44,000 to 87,000 psi) transmitted by water at temperatures in a range of 4° C. to 10° C. or alternately at ambient temperature. In the case of the present invention this is expected to extend the product life to 7 to 10 days. Where the "milk" is subjected to high levels of carbon dioxide, such as with supercritical fluid (SCF) $CO_2$, the solution may be handled at temperatures as low as 35° C. or 40° C., and at lower pressures, e.g., 73 atmospheres or 7.4 MPa of pressure. The SCF $CO_2$ route further aids rupturing, provides complementary extraction, is an excellent sanitizer, remains below denaturation temperatures, and can be used at substantially lower pressures than HPP, moreover any carbon dioxide residues after processing are relatively non-toxic thus it is safe as a solvent.

Combination Regimes.

A particularly useful variation for co-extracting is as follows, though the invention is not so limited for combinations. First, a fresh culture of Lion's Mane is extracted in a single pass. The solid residue from the first pass is then combined with fresh material from a second fungal species including the substrate from the growth culture of that second species, and an additional extraction is performed on that two-species sample. Liquid from the first pass may be used to make a preparation to administer Lion's Mane alone. And liquid from the second pass may be used to make a preparation to administer the combination of Lion's Mane and the second species. Second species that have been found to work well by this method include Reishe, Turkey Tail and Shiitake, but the invention is not so limited.

Medicinal Context for Lion's Mane.

The species Lion's Mane, *Hericium erinaceus*, was selected as suitable for the current work because its relative potency from traditional preparations is known and because it has promise for important future use. Lion's mane is used in traditional Chinese medicine. It is reported that pills of this mushroom are used to treat gastric ulcers and esophageal carcinoma. A 2005 study in rats showed that some of the more universal compounds of the mushroom, e.g., threitol, D-arabinitol and palmitic acid, may have antioxidant effects, may regulate blood lipid levels and may reduce blood glucose levels.

However the neuroprotective effects are the most intriguing. About a dozen studies have been published on the neuroregenerative properties of lion's mane mushrooms since Kawagishi first identified NGFs in Japanese samples in 1991. Two novel classes of Nerve Growth Factors (NGFs)— molecules that stimulated the differentiation and re-myelination of neurons—have been discovered in this mushroom so far and validated both in vitro and in vivo. These cyathane derivatives are termed "hericenones" and "erinacines." Our measurements find that their levels can vary substantially between fungal strains.

Lion's mane (also called Yamabushitake) has been investigated for anti-dementia effects and validated for reversal of mild cognitive impairments in animals. Lion's mane stimulates animal nerve cells, nerve growth in vitro and myelination in vitro. In 2009, researchers at Hokuto Corporation and the Isogo Central and Neurosurgical Hospital published a small clinical study in which 30 Japanese patients with mild cognitive impairment received significant benefits for as long as they consumed the mushrooms. There they took four 250 mg tablets containing 96 percent of Yamabushitake dry powder three times a day for 16 weeks. After termination of the intake, the subjects were observed for the next four weeks. At weeks eight, 12 and 16 of the trial, the Yamabushitake group showed significantly increased scores on the cognitive function scale compared with the placebo group. The Yamabushitake group's scores increased with the duration of intake, but at week four after the termination of the 16 weeks intake, the scores decreased significantly. (Mori, 2009)

Recently, mice were injected with neurotoxic peptides in an experiment to assess the effects of lion's mane on the type of amyloid plaque formation seen in Alzheimer's patients. The mice were then challenged in a standard "Y" maze, designed for testing memory. Mice fed with a normal diet were compared to those supplemented with lion's mane mushrooms. As the peptide-induced plaque developed, the mice lost the ability to memorize the maze. When these memory-impaired mice were fed a diet containing 5 percent dried lion's mane mushrooms for 23 days, the mice performed significantly better in the Y maze test. Interestingly, the mice regained another cognitive capacity, something comparable to curiosity, as measured by greater time spent exploring novel objects compared to familiar ones.

The reduction of beta amyloid plaques in the brains of mushroom-fed mice vs. the mice not fed any mushrooms was remarkable. The formation of amyloid plaques is what many researchers believe is a primary morphological biomarker associated with Alzheimer's. Plaques linked to beta amyloid peptide inflame brain tissue, interfere with healthy neuron transmission, and are indicated in nerve degeneration.

Bibliography for Lion's Mane

Kawagishi, H., Ando, M., Sakamoto, H., Yoshida S., Ojima, F., Ishiguro, Y., Ukai, N., Fukukawa, S, 1991. "Hericenone C, D and E, stimulators of nerve growth factor (NGF) synthesis from the mushroom *Hericium erinaceum*." Tetrahedron Lett 32, 4561-4564.

Ma, Bing-Ji, Jin-Wen Shen, Hai-You Yu, Yuan Ruan, Ting-Ting Wu & Xu Zhao, 2010. "Hericenones and erinacines: stimulators of nerve growth factor (NGF) biosynthesis in *Hericium erinaceus*." Mycology: An International Journal on Fungal Biology. 1(2): 92-98.

Mori, K., Inatomi, S., Ouchi, K. Azumi, Y and Tuchida T. 2009. "Improving effects of the mushroom Yamabushitake (*Hericium erinaceus*) on mild cognitive impairment: a double blinded, placebo controlled clinical trial." Phytother Res. 23:367-372.

Mori, K., Obara, Y., Moriya, T., Inatomi, S., Nakahata, N. 2011. "Effects of *Hericium erinaceus* on amyloid β(25-35) peptide-induced learning and memory deficits in mice." Biomed Res. 32 (1):67-72.

Nagano, M., Shimizu, K., Kondo, R., Hayashi, C., Sato, D., Kitagawa, K., Ohnuki, K. 2010. "Reduction of depression and anxiety by 4 weeks *Hericium erinaceus* intake." Biomed Res. 31(4):231-7.

Stamets, P., "Notes on nutritional properties of culinary-medicinal mushrooms." International Journal of Medicinal Mushrooms. 2005; 7:109-116.

Thal, L. J., Kantarci, K., Reiman, E. M., Klunk, W. E., Weiner, M. W., Zetterberg, H., Galasko, D., Pratico, D., Griffin, S., Schenk, D., Siemers, E. 2006. "The role of biomarkers in clinical trials for Alzheimer disease." 20(1): 6-15.

Medicinal Context for Reishi.

The species known as Reishi (i.e., *Ganoderma lucidum* or "lingzhi") was selected as suitable for the current work because, as for lion's mane, its relative potency from traditional preparations is known and because it has promise for important future use.

Lingzhi has anti-tumor, anti-cancer, immunomodulatory and immunotherapeutic properties, as reported by various studies on the polysaccharides, terpenes, and other bioactive compounds that have been isolated from it fruit bodies and mycelia. Reviews by R. R. Paterson and by Lindequist et al. have more details. It has also been reported to inhibit platelet aggregation, and to lower blood pressure (via inhibition of angiotensin-converting enzyme), cholesterol, and blood sugar.

Laboratory studies have shown anti-neoplastic effects of extracts or isolated compounds from reishe against some types of cancer, including epithelial ovarian cancer. In an animal model, *Ganoderma* has been reported to prevent cancer metastasis, with potency comparable to that of Lentinan from Shiitake mushrooms. The anti-cancer mechanisms are unknown but may target a variety of stages of cancer development: angiogenesis mediated by cytokines; cytoxicity; metastasis, inhibition; apoptosis of tumor cells. Nevertheless, *Ganoderma lucidum* extracts are employed in commercial drugs such as MC-S to suppress cancer cell proliferation and migration.

Some studies have found that ganoderic acid is protective in mice against liver injury by viruses and other toxic agents, thus it may have similar benefits for humans. Also, *Ganoderma*-derived sterols inhibit lanosterol 14α-demethylase activity in cholesterol biosynthesis, and *G. lucidum* compounds inhibit 5-alpha reductase activity in dihydrotestosterone biosynthesis. *G. lucidum* is also reported to have anti-bacterial and anti-viral activities, including against the following: HSV-1, HSV-2, influenza virus, vesicular stomatitis. *G. lucidum* mushrooms are also reported to be anti-fungal against *Aspergillus niger, Bacillus cereus* and *Candida albicans*, and to be anti-bacterial against *Escherichia coli*. Other potential benefits of ganoderic acid include lowering hypertension, reducing cholesterol, and anti-inflammatory benefits. The *G. lucium* genome, with about 12,600 genes on 13 chromosomes, was sequenced in 2012.

Traditional preparations are made by simmering thinly sliced or pulverized lingzhi (either fresh or dried) in a covered pot of simmering water for two hours. The resulting liquid is dark and bitter (inedibly bitter for red lingzhi, as opposed to the less active black lingzhi that may be used in soups). The process may be repeated to further concentrate the active ingredients. Or the liquid may be added to a decoction or an extract (in liquid, capsule, or powder form). The hot water process extracts the polysaccharides; alcohol extracts the medicinal triterpenes.

Bibliography for Reishi

Jones, Kenneth (1990), *Reishi: Ancient Herb for Modern Times*, Sylvan Press, p. 6.

Karsten P A. (1881). "Enumeratio Boletinearum et Polyporearum Fennicarum, systemate novo dispositarum". *Revue mycologique, Toulouse* (in Latin) 3 (9): 16-19.

Liddell, Henry George and Robert Scott (1980). *A Greek-English Lexicon (Abridged Edition)*. United Kingdom: Oxford University Press. ISBN 0-19-910207-4.

R. S. Hseu, H. H. Wang, H. F. Wang and J. M. Moncalvo (1 Apr. 1996). "Differentiation and grouping of isolates of the *Ganoderma Lucidum* complex by random amplified polymorphic DNA-PCR compared with grouping on the basis of internal transcribed spacer sequences" (Abstract). *Appl. Environ. Microbiol.* 62 (4): 1354-1363. PMC 167902. PMID 8919797.

Pregadio, Fabrizio (2008). "Zhi 芝 numinous mushrooms; excrescences", in *The Encyclopedia of Taoism*, Fabrizio Pregadio, ed., Routledge, p. 1271.

Tr. by E. Bretschneider (1893), *Botanicon Sinicum; Notes on Chinese Botany from Native and Western Sources*, Kelly & Walsh, p. 40.

Groot, Jan Jakob Maria (1892-1910), *The Religious System of China: Its Ancient Forms, Evolution, History and Present Aspect, Manners, Customs and Social Institutions Connected Therewith*, Brill Publishers, Vol. IV, p. 307.

David Arora (1986). *Mushrooms Demystified, 2nd edition*. Ten Speed Press. ISBN 0-89815-169-4.

Pregadio (2008), p. 1271.

Hu, Shiu-ying (2006), Food plants of China, Chinese University Press.

Bedini, Silvio A. (1994), The Trail of Time, Cambridge University Press, p. 113.

Knechtges, David R. (1996), 'Wen Xuan or Selections of Refined Literature, Volume III, Princeton University Press, p. 211.

Schipper, Kristofer M. (1993). The Taoist Body, University of California Press, p. 174. *Oxford English Dictionary* (2009), CD-ROM edition (v. 4.0), s.v. ling chih.

Stephen Wootton Bushell (1904), *Chinese Art*, Victoria and Albert Museum, p. 148. This context describes the lingzhi fungus and ruyi scepter as Daoist symbols of longevity on a jade vase.

Names of a Selection of Asian Fungi, multilingual multi-script plant name database. http://www.dl.begellhouse.com/journals/708ae68d64b17c52, 72e9ed69099c0eef,6b7a7dab0ec964e7.html Paterson R R (2006). "*Ganoderma*—a therapeutic fungal biofactory". *Phytochemistry* 67 (18): 1985-2001. doi: 10.1002/chin.200650268. PMID 16905165.)

Biosci. Biotechnol. Biochem., 68 (4), 881-887, 2004

*Medicinal Mushrooms: An Exploration of Tradition. Healing, & Culture* (Herbs and Health Series) by Christopher Hobbs (Author). Harriet Beinfield (National Audubon Society; Field Guide to Mushrooms, 1993) Pre-Qin and Han texts, Chinese Text Project.

Unschuld, Paul U. (1985), *Medicine in China: A History of Ideas*, University of California Press, p. 112.

Tr. by Legge, James (1885), *The Li Ki,* 2 vols, Oxford University Press, vol. 1, p. 461.

Tr. by Hawkes, David (1959), *Ch'u Tz'u: The Songs of the South*, Clarendon, p. 258.

Tr. by Major, John S., Sarah Queen, Andrew Meyer, and Harold D. Roth (2010), *The Huainanzi: A Guide to the Theory and Practice of Government in Early Han China*, Columbia University Press, p. 634.

Tr. Knechtges (1996), 201.

神農本草經，草上品。赤芝。，苦，平，無毒。胸中結，益心氣，補中，增智慧，不忘。久食，輕身不老，延年神仙。，一名丹芝。，延年神仙。

Tr. by Yang Shouzhong (1998) *The Divine Farmer's Materia Medica: A Translation of the Shen Nong Ben Cao Jing*, Blue Poppy, pp. 17-18

Reishi mushroom, Reishiessence.com.

抱朴子／卷 11; tr. by Ware, James R. (1966). *Alchemy, Medicine and Religion in the China of A. D.* 320: The Nei Pien of Ko Hung. Dover. pp. 258.

Medicinal Context for Turkey Tail.

The polypore species known as Turkey Tail (*Trametes versicolor*) is a common mushroom found throughout the world. It was selected as suitable for the current work because of its promise for important future use, for instance its glycoprotein component known as PSK was the object of 25% of Japan's total national expenditure on anticancer agents in the late 1980's. The raw mushroom is not potent as an anti-cancer agent, but its glycoprotein, "Polysaccharide K" (PSK; Krestin) has displayed anticancer activity in vitro, in vivo and in preliminary clinical studies, and is used as an anticancer immunologic adjuvant in some countries. Some findings indicate that PSK may help prevent the formation and recurrence of cancers induced by mutagens, radiation and spontaneous formation. PSK is a known beneficial adjuvant for treatment of gastric, esophageal, colorectal, breast and lung (both small-cell and non-small cell carcinomas) cancers. In vitro studies of PSK in combination with lentinan and other fungal compounds may inhibit proliferation of cancer cells. The medical science is still at an early stage, and the underlying mechanisms have not been elucidated yet. PSK is present in the CM-101 strain of Turkey Tail; an analogous compound PSP (Polysaccharide Peptide) is present in the COV-1 strain.

Medicinal Context for Shiitake.

The species known as Shiitaki (*Lentinus edodes*) is an edible mushroom native to East Asia and has several aliases arising from its growth on oak substrates; currently this species accounts for 25% of commercial mushroom production worldwide. Its medicinal history dates back to the Ming Dynasty, when it was documented for uses for upper respiratory diseases, poor blood circulation, liver trouble, fatigue, weakness and premature aging, among other disorders. In modern times the beta-glucan polysaccharide lentinan has been isolated from shiitake and used for instance with PSK as noted above for antiproliferation compositions for cancer. One shiitake molecular component, eritadenine, has been shown to have hypocholesterolemic activity and to inhibit S-adenosyl-L-homocysteine hydrolase (SAHH) enzyme. Another component, "active hexose-correlated compound" (AHCC), is Japan's second most popular complementary medication for cancer and appears to enhance immune function as well as acting on at least hepatocellular carcinoma and prostate cancer. Other research is evaluating AHCC's ability to boost resistance to bacterial and viral pathogens and to reduce platelet aggregation.

Medicinal Context for Portobello.

This basidiomycete species is an edible mushroom native to North America and Europe but grown around the world. It is widely known as Button/Portobello/Crimini (*Agaricus bisporus*) but has many other names, depending on whether it is of the white or brown type and whether it is in its immature or mature form. Its mature form is called Portobello. The main nutritional compounds are in the form of Vitamin D2, sodium, potassium, phosphorus, conjugated linoleic acid, antioxidants, protocatechuic acid and pyrochatecol. In one study a diet of fresh mushrooms was reported to reduce the incidence of breast cancer in women by 64%, and by almost 90% when green tea was also in the diet. One component, 2-aminophenoxazine-3-one, is known to be an aromatase inhibitor, i.e., appears to act directly upon breast cancer and ovarian cancer. Properties that boost immunity have been found, and an in vitro study demonstrated enhanced dendritic cell function. Curiously these mushrooms appear to fuel an increase of tumors in the bone, stomach and lungs in animal studies yet hydrazine components such as agaritine have no significant toxicity to human subjects; it may be that their anticarcinogenic effects arise by induction of apoptosis.

Medicinal Context for Royal Sun Agaric.

The species known as Royal Sun Agaric (*Agaricus subrufescens/blazei* Murrill/*brasiliensis/rufotegulis*) has several common names such as almond mushroom, mushroom of the sun, God's mushroom, mushroom of life, royal sun *agaricus*, jisongrong and himematsutake. It is widely used for both edible and medicinal benefits. The species has oncotherapy benefits that are believed to arise from its high level of beta glucans; by contrast its immunity-boosting properties are believed to arise from its alpha glucans. In any case it is Japan's most popular complementary medicine for cancer, and is also important in Brazil. There is some variability in results, so the commercial source is important; U.S. Pat. No. 6,120,772 to Hitoshi and Toshimitsu reports a hybrid that is up to 3,000 times more potent than the native species. In any case the native species is well known to stimulate immune system cells and production of immune system cytokines such as interferons and interleukins. Cell and animal studies have shown that the mushroom has effects against the following types of cancer, which depending on the cancer affected growth, proliferation, metastasis, apoptosis, or another aspect of the cancer: colorectal; fibrosarcoma; sarcoma; gynecological; ovarian; lung; leukemia; myeloma; hepatocarcinoma; stomach; prostate; and skin. Whether it has antiviral properties is unclear, but it has beneficial effects on inhibiting pathogens and angiogenesis. This species also has benefits for lowering blood glucose levels and improving insulin resistance. It also lowers cholesterol, increases metabolism of fats, increases muscle mass, likely due to conjugated linoleic acid (CLA).

Medicinal Context for Enoki.

The species known as Enoki or enokitake (*Flammulina velutipes/populicola*), has various names, including (in cultivation) golden needle or lily mushroom and (for forms in the wild) seafood mushrooms, winter mushrooms or winter fungus, and velvet foot/stem/shank. Animal testing has suggested these mushrooms may have applications for use for vaccines and cancer immunotherapy. The stalk is rich in a protein called FIP-fve or Five for immunoregulation. Another component is flammutoxin protein, which is cytolytic, cardiotoxic, yet orally non-toxic. Enoki extracts also contain antioxidants such as the compound ergothioneine. Six weeks of dietary supplements of erothioneine have been reported to reduce pain and increase the subject's range of movement. The exact effect of ergothioneine is not known in humans, but it has a specific transporter (ETT) into human cells. And ETT mutants are associated with autoimmune disorders such as rheumatoid arthritis and Crohn's disease.

Medicinal Context for Maitake.

The polypore species known as Maitake (*Grifola frondosa*) is native to North America and Northeastern Japan and has several common names such as hen-of-the-woods, ram's head, sheep's head and signorina. Its key nutrient value includes for vitamins $B_2$, $D_2$ and niacin as well as for potassium, calcium, magnesium, amino acids and fiber. The species is used in Chinese and Japanese medicine to enhance the immune system and as a regulator for: blood pressure, glucose (hypoglycemic effect; alpha glucosidase inhibitor), insulin, serum lipids, liver lipids (cholesterol, triglycerides, phospholipids) and weight loss. At least one of the active constituents is a beta glucan conjugated to a protein. Clinical trials showed relatively recently that Maitake stimulates both the innate and adaptive immune systems and for instance, NK cells. Moreover Maitake has anti-cancer activity, which may be due to its known activity in: induction of some cancer cell lines; growth inhibition for some cancer cell lines; and/or inhibition of angiogenesis by inhibiting vascular endothelial growth factor (VEGF). Potential antimetastatic properties have been observed during in vitro studies. Maitake also contains antioxidants and may partially inhibit the enzyme cyclooxygenase.

Medicinal Context for Oyster Mushrooms.

The species known as Oyster Mushrooms (*Pleuroyus ostreatus/pulmonarius*) has certain promising medicinal properties. Alcohol-soluble extracts specifically inhibit growth of colon and breast cancer cells without significantly affecting normal cells, and they have a potential therapeutic/preventive effect on breast and colon cancer, and were more effective than alcohol-soluble extracts of button [i.e., portobello], shiitake and enoki mushrooms. Oyster mushroom extracts up-regulate genes coding for p53 and p21 proteins, halting tumor growth and supporting tumor regression. Non-alcohol soluble beta glucan and glycoprotein complexes in oyster mushrooms activate the immune system's natural killer and cytotoxic T cells against cancer. Oyster mushroom mycelia can also kill and digest nematodes as well as pathogenic bacteria (*Pseudomonas, Agrobacterium*). And exudates of this mushroom are antibiotic toward and inhibit a wide range of gram-negative bacteria (including *Salmonella, Pseudomonas, E. coli*, and *Staphylococcus aureus*). Also, ingestion of oyster mushrooms and their beta-glucans is thought to reduce blood triglycerides and LDL blood cholesterol levels. Oyster mushrooms are also an excellent source of natural lovastatin for cardiovascular benefits.

Medicinal Context for *Rhizopus oligosporus*.

Although several other *Rhizopus* species are problematic, the filamentous fungal species *R. oligosporus* is widely used for soybean fermentation, specifically to make tempeh. Typically, with aid from lactic bacterial inoculums, *R. oligosporus* is cultured with legumes (or grains) that have been soaked, peeled, parboiled, with the result that it forms a compressed cake of mycelia, which are edible as live cultures. The fungus has several features of interest. *R. oligosporus* releases enzymes that make proteins more digestible. Upon ingestion it produces an antibiotic against gram-positive bacterial pathogens such as *Staphylococcus aureus* (but also hinders beneficial species such as *Bacillus subtilis*), reducing intestinal infections. Other effects include inhibiting tumor development, lowering cholesterol and decreasing diarrhea issues. It also reduces iron-deficient anemia, lipid oxidation and hypertension. Cultures also contain provitamin D2 and vitamin B12.

As seen above for *R. oligosporus*, useful fungi for the invention are not limited to mushrooms but can also include cultures of mycelia, and by extension microfungi. In fact, to the extent that cultures are harvested at the mycelia stage, the distinction between macro- and microfungi is largely immaterial, indeed the microfungal designation is more descriptive than taxonomical because microfungal species occur in numerous genera that also have macrofungi, and/or as alternate morphologies for macrofungal species. In addition, the invention contemplates use with single-celled fungi also. Single-celled fungi are known generally as yeasts regardless of their taxonomic classification; the following section addresses the medicinal interest of edible single-celled fungal species.

Medicinal Context for *Saccharomyces cerevisiae*.

Separate variants of *S. cerevisiae* are known as brewer's yeast and bakers yeast, and their history of human use goes back at least to ancient Egypt. Brewer's yeast has been shown to rapidly escalate apoptosis of metastatic breast-cancer cells that engulf them by phagocytosis: within 30 minutes, 13% of metastatic cells died, and 38% perished within four hours. This represents more than six times greater apoptosis than for normal engulfed cells, and almost triple the normal apoptosis rate for metastatic breast cancer cells generally. Ingestion of brewer's yeast has also been shown to reduce the symptoms of premenstrual syndrome by more than 80%. Probiotic use of brewer's yeast is also known to reduce the incidence and duration of antibiotic-associated diarrhea, especially for the refractory pathogen *Clostridium dificile*. Moreover regular ingestion has been shown to reduce cold and flu symptoms by 16% and to reduce duration of those diseases by 11%. And Brewer's yeast is a common nutritional supplement for chromium, selenium, proteins and B-complex vitamins, in part because the chromium content potentiates human insulin receptors, decreases insulin resistance and increases pancreatic beta-cell function.

Medicinal Context for *Saccharomyces boulardii*.

Like *S. cerevisiae* the yeast *S. boulardii* is used probiotically to maintain and restore natural gastrointestinal flora thus addressing symptoms of acute diarrhea, reducing infection risk from *Clostridium difficile*, reducing bowel movements in patients having diarrhea-predominant irritable bowel syndrome (IBS), addressing other inflammatory bowel diseases, preventing relapse of Crohn's disease when in remission, reducing symptoms of patients who have ulcerative colitis and reducing incidence of antibiotic-, traveler's-, and HIV/AIDS-associated diarrheas. Regarding *C. difficile*, *S. boulardii* secretes a protease in vivo that degrades two of its exotoxins and inhibits their binding to receptors along the brush border. *S. boulardii* also binds the cell surfaces of pathogens *Escherichia coli* and *Salmonella typhimurium*, preventing their binding to the brush border also. Other pathogens hobbled by *S. boulardii* include *Vibrio cholera* (cholera). The anti-inflammatory properties of *S. boulardii* arise from its ability to inhibit key pro-inflammatory cytokines. It is also able to trigger an immune response by inducing secretion of immunoglobulin A in the small intestine.

Medicinal Context for *Monascus purpureus*.

*M. purpureus* is a yeast classified as a mold, and is responsible for the production of red rice koji (in Japan), also known as red yeast rice (in China), i.e., rice overgrown with the mold. This product traces its roots at least as far back as 300 B.C. *M. purpureus* is of particular interest because it is a natural source of monacolin K, which is identical to lovastatin, a commercial drug that blocks cholesterol synthesis by inhibiting HMG-CoA reductase, thereby reducing the total cholesterol, "bad" LDL-cholesterol (e.g., by about 20%) and triglycerides in circulation, and increasing "good" HDL cholesterol. The "Went" strain of *M. purpureus* produces 0.4% monacolin K; 1.2 g to 1.4 g/day at that level provides about 10 mg of total monacolins (which includes monacolin K, L and J), of which 5 mg is monacolin K. This is somewhat lower than prescription levels of Lovastatin, which are typically in a range of 20-80 mg/day. However based on controls, China Coronary Secondary Prevention Study (CCSPS) of 5,000 post-heart-attack patients for an average of 4.5 years using a 0.8% total monacolin content ethanol extract of red yeast rise found risk was reduced by 45% for follow-on heart attacks, by 31% for cardiovascular-based deaths and by 33% for death from any cause. This is in fact better than clinical observations for prescription lovastatin, thus there may be roles for other native constituents such as phytosterols. The related fungi *Monascus ruber* and *Monascus pilosus* are also used in industrial applications.

The invention is not intended to be limited to the species described above; they are merely illustrative. As examples of other important mushrooms, *Schizophyllum commune* produces a beta glucan, schizophyllan, that is normally provided in a clinical setting by intramuscular or intraperitoneal administration, and which has been shown to be cytostatic in Sarcoma 180 tumors. Similarly, *Phellinus linteus* has long been used in traditional Chinese medicine in the form of hot water extracts from the fruit bodies. Those preparations have more recently reported to improve symptoms of digestive system cancers such as esophageal, duodenal, colorectal, as well as hepatocellular cancers, and have also been reported to impart a greater feeling of well-being, generally in combination with conventional chemotherapy in an adjuvant or neo-adjuvant setting. Another example is the chaga mushroom (*Inonotus obliquus*), which is prominent in Russian medicine and is found in the birch forests of Asia, Europe and North America. It is an antioxidant and anti-inflammatory agent, and has shown potential for cancer therapy and immunotherapy.

Further examples are shown below for non-cancer indications including cardiovascular and glycemic therapies, where the diversity and additional species are evident in even a relatively short published catalog of important macrofungi (i.e., fungi whose fruit bodies are visible to the eye). See Richard Sullivan, John E. Smith and Neil J. Rowan, *Medicinal Mushrooms: Their therapeutic properties and current medical usage with special emphasis on cancer treatments*, (2002) at pp. 184-185 posted at http://www.academia.edu/305933/Medicinal_Mushrooms_Their_therapeutic_properties_and_current_medical_usage_with_special_emphasis_on_cancer_treatments.

Illustrative macrofungi with effects on cardiovascular health are shown below, where "X" indicates the effect:

| | Causes reduction of: | | | | |
|---|---|---|---|---|---|
| Species | Total cholesterol | "Bad" cholesterol | Triglycerides | Blood platelet binding | Arterial blood pressure |
| *Auricularia auricular-judae* | X | X | | X | |
| *Calyptella* sp. | | | | X | |
| *Cordyceps sinensis* | X | | X | | |
| *Ganoderma lucidum* | X | | | X | X |
| *Grifola frondosa* | X | | X | | X |
| *Kuehneromyces* sp. | | | | X | |
| *Lentinus edodes* | | | X | | |
| *Neolentinus adhaereus* | | | | X | |
| *Panus* sp. | | | | X | |
| *Pleurotus ostreatus* | X | | | | |
| *Tremella fuciformis* | X | X | | | |
| *Tricholoma mongolicum* | | | | | X |

Illustrative macrofungi with effects on glycemic health are shown below, where "X" indicates the effect:

| | Active against: | | |
|---|---|---|---|
| Species | Insulin-dependent diabetes | Non-insulin-dependent diabetes | Only in non-diabetic animals |
| *Agaricus bisporus* | X | | |
| *Agrocybe aegerita* | X | | |
| *Coprinus comatus* | | | X |
| *Cordyceps sinensis* | X | | |
| *Grifola frondosa* | | X | |
| *Tremella aurantia* | X | | |

The invention may be further understood through the following examples. The examples are intended to be illustrative but not limiting as to the scope and practice of the invention.

Preparatory Example

Emulsions were prepared as described above, i.e., parboiled rye grain was tossed with the mineral supplement; Lion's Mane and Reishi were grown on the medium until their primordial stage, then shipped, refrigerated, blended and filtered to obtain an emulsion as stated above.

Medicinal Example 1: Parkinson's Disease

A male subject, white, age 64, had a ten-year history of Parkinson's disease. This was complicated by an incident of heavy metal poisoning 6 years before the start of the clinical trial, due to the use of contaminated herbal medicines to treat his Parkinson's disease. A further complication was Lyme disease contracted 2 years before the start of the clinical trial. He had never been treated with allopathic drugs for any of these conditions.

For the two-year period leading up to the clinical trial the subject's overall health had been in rapid decline. His speech had been deteriorating rapidly during this period and had become almost unintelligible whispers; excessive drooling further interfered with his articulation. The subject had required assistance to sit down in and to stand up from his wheel chair for all of the two-year period and had been unable to ascend stairs for over two years. He had also had increasing difficulty chewing and digesting food.

During the trial this subject received a 3-ounce daily dose of a Lion's Mane emulsion according to the invention, made fresh every three days. All of the subject's caretakers—including a board-certified physician, physical therapists and licensed massage therapists—kept meticulous weekly records of all observed effects. Within the first week, his family noticed an improvement in the subject's speech, energy, and clarity of thought. After two months on the daily dose, the subject could seat himself in and rise from his wheel chair by himself. At about that same time, he began ambulating unassisted. After three months on the daily dose the subject was speaking in a normal, intelligible, robust voice. After four months on the daily dose the subject had sufficient stamina to travel by car to visit family members—formerly impossible due to his lack of energy—and he was independently climbing stairs to enter the second floor of his home. Over the following year the course of medicinal treatment was discontinued and the subject began a low dose treatment with commercial prescription products. His response to the follow-on treatment was substantially better than the prognosis, which may suggest that the emulsions had an adjunctive benefit.

Medicinal Example 2: Fahr's Disease

A male subject, white, age 60, had a known diagnosis of Fahr's disease. Fahr's disease is a rare, genetic disease, autosomal dominant, characterized by calcification of the basal ganglia. It is idiopathic, has no known cure, and is marked by an inexorable insidious loss of neurological function, similar to ALS (i.e., Lou Gehrig's disease). Before beginning the clinical trial the subject was almost unintelligible even to a listener only 12 inches away. The subject was receiving no other conventional medical treatments at the time. For the clinical trial the subject received combination of 3-ounce daily dose of an emulsion according to the invention for Lion's Mane and a 3-ounce daily dose of Reishi emulsion according to the invention. Within one week of the onset of treatment the subject's speech had become clear and strong, as if normal. Over the following year product use was discontinued, however the subject continued to function substantially better than his prognosis indicated.

Medicinal Example 3: Metastatic Kidney Cancer

A female subject, white, age 63, had recurrent metastatic renal cell carcinoma. Under the care of university oncologists who did not know the drug's identity she was in a blind clinical trial and received a 3-ounce daily dose of a Lion's Mane emulsion according to the invention, made fresh every three days. It appears that the active compounds spontaneously concentrated in the areas of her known tumor metastasis. During the first 5 months of receiving daily doses without fail, her monthly scans remained stable and there was no sign of further metastasis or tumor growth. In the following year serial scans revealed minor tumor growth but no other spread of the cancer, and the patient's state of health and comfort has remained substantially better than otherwise expected.

Medicinal Example 4: Depression

A female subject, white, age 68, had a 5-year history of chronic clinical depression, insomnia and severe anxiety; the subject also had substantial psycho-motor retardation as a result. Due to physiological intolerances she had been unable to receive standard treatments for these conditions. During the clinical trial this subject received a 3-ounce daily dose of a Lion's mane emulsion according to the invention, made fresh every three days. Dosing of the subject was intermittent due to limited supply and interrupted delivery of the emulsions. When doses were available the subject's recovery was consistently rapid, remarkable and apparently complete. During periods when doses were unavailable, after a few days without a dose the patient consistently relapsed, but recovered very rapidly upon resuming the doses. This pattern has continued to be observed for over one year.

Medicinal Example 5: Multiple Sclerosis

A female subject, white, age 56, had a five-year history of Multiple Sclerosis (MS). The condition had not been treated with drugs. The patient received 3 ounces daily of a Lion's Mane emulsion according to the invention. Within a week of beginning treatment, her medical caretakers observed distinct improvements in her balance and ambulatory abilities.

Medicinal Example 6: Fatigue from Metastatic Breast Cancer

A female subject, white, age 55, had stage IV metastatic breast cancer, had an ongoing course of chemotherapy, and was consequently severely fatigued. The subject also had partial alopecia on her scalp due to the chemotherapy. She received 1.5 oz. twice daily of Reishi extract emulsion according to the invention, which alleviated her fatigue essentially completely. When the subject ceased taking the doses for several days her fatigue returned to a severe degree, and the condition abated again when she resumed the doses. It was also observed that marked growth of new hair coincided with treatment with the extract.

Medicinal Example 7: Chronic Pain and Fatigue

A male, white, age 40, had been in long-time therapy for chronic pain due to breakage of a vertebra 25 years before. His regular course of treatment for pain management included epidural nerve block medications, pain relief medications, regular physical therapy and acupuncture. The subject then began taking a 1.5-oz. daily course of Lion's Mane extract emulsion according to the invention together with his regular medicinal regimen. Within one week of treatment his muscle spasms ceased and the muscles relaxed, and the pain was almost unnoticeable. Within one month after beginning the extract regime he terminated use of his other medications and physical treatments, and for medicinal benefit was relying entirely upon the daily 1.5 oz. dosing of Lion's Mane extract and was essentially free of pain. The subject also reported that taking the extract doses in the evening after work during the first week of treatment with Lion's Mane gave him a feeling of energy, well-being and removed his desire for sleep despite full days of work and activity as a full-time single father of two boys. Daily administration of the extract was then shifted to the morning after rising; the subject reported that this resulted in marked alertness throughout the day and sound sleep at night.

Medicinal Example 8: Disability from Lupus and Fibromyalgia

A female, white, age 35, had been diagnosed with lupus and fibromyalgia. As one result of her condition she had been unable to perform ordinary manual tasks for the previous two years, such as removing the cap from a sealed bottle of water. The subject began taking a daily dose of 1.5 ounce of Lion's Mane raw cytoplasm emulsion according to the invention. Within three days after beginning this course of treatment her hands had recovered sufficiently that she was able to remove the caps from several sealed bottles of water in sequence. The subject continued the course of treatment for several months, and remained capable and dexterous. Upon discontinuation of the Lion's Mane extract her symptoms returned within a few days. Two weeks after treatment stopped she resumed it, and within three days after resuming her manual symptoms were abated again.

Medicinal Example 9: Depression and Anxiety Disorders

A male, white, age 50, had a long history of anxiety attacks and depression attributed to post-traumatic stress disorder. His condition further included a sleep disorder and bipolar tendencies. To address the symptoms the subject had a history of self-medicating with cannabinoids. Then the subject began receiving 8-ounce daily doses of a combination emulsion of Lion's Mane, Reishi and *Agaricus bisporus* extracts according to the invention, where the extract of each respective species was approximately equally represented in the cocktail. The subject reported that within two months he no longer felt the need to self-medicate; and upon ceasing use of cannabinoids he experienced no ill effects or withdrawal symptoms. The subject has now had two years' of ongoing Lion's Mane and Reishi combination therapy using emulsions according to the invention, and has a positive outlook without relapse into depression, anxiety attacks or sleep disorder.

The embodiments of the invention as described herein are merely illustrative and are not exclusive. Numerous additions, variations, derivations, permutations, equivalents, combinations and modifications of the above-described invention will be apparent to persons of ordinary skill in the relevant arts and are within the scope and spirit of the invention. The invention as described herein contemplates the use of those alternative embodiments without limitation.

The invention claimed is:

1. A process for preparing high-potency fungal medicinal materials comprising the steps of:
   a) growing organisms from a medicinal fungal species in a culture on a cell-based growth medium, wherein:
      i) the fungal species is a species that is edible when raw; and
      ii) the cell-based growth medium is edible;
   b) placing at least a portion from the fungal organisms and at least a portion from the cell-based growth medium into an extraction medium; thereby forming a biomass processing medium, wherein the extraction medium is edible and or potable; and
   c) in the biomass processing medium, rupturing substantially all cells of the fungal organisms and the growth medium cells that had been placed therein, thereby forming a medicinal composition, wherein;
      i) the medicinal composition comprises each of the following: contents from the ruptured fungal organisms, contents from the medicinal composition, and the extraction medium;
      ii) the medicinal composition is edible and or potable; and
      iii) enzymes and other proteins from the fungal organisms of step (a) remain largely undenatured throughout each of steps (a), (b), and (c).

2. The process of claim 1 wherein the rupturing is performed by a mixer blade.

3. The process of claim 2 wherein the cells are present in an extraction medium that comprises water and an edible oil while the rupturing is performed by the mixer blade.

4. The process of claim 3 wherein the rupturing is performed in an extraction medium at a temperature that is between 0° C. and 40° C., a pH that is between 4 and 10, inclusive; and the extraction medium is substantially free of denaturing compounds that are not generated by the cells themselves.

5. The process of claim 1 wherein the contents of the ruptured cells are subjected to a high-pressure treatment following the rupturing.

6. A pharmaceutical composition that is made by a process for preparing high-potency fungal medicinal materials; wherein the process comprises the steps of:
   a) growing organisms from a medicinal fungal species in a culture on a cell-based growth medium, wherein:
      i) the fungal species is a species that is edible when raw; and
      ii) the cell-based growth medium is edible;
   b) placing at least a portion from the fungal organisms and at least a portion from the cell-based growth medium into an extraction medium, thereby forming a biomass processing medium, wherein the extraction medium is edible and or potable; and
   c) in the biomass processing medium, rupturing substantially all cells of the fungal organisms and the growth medium cells that had been placed therein, thereby forming a medicinal composition, wherein:
      i) the medicinal composition comprises each of the following: contents from the ruptured fungal organisms, contents from the medicinal composition, and the extraction medium;
      ii) the medicinal composition is edible and or potable; and
   enzymes and other proteins from the fungal organisms of step (a) remain largely undenatured throughout each of steps (a), (b), and (c).

7. The composition of claim 6 wherein the fungal species is selected from the group consisting of macrofungi, microfungi and single-celled fungi.

8. The composition of claim 6 wherein the fungal species is selected from the group consisting of the following species: *Agaricus bisporus; Agaricus blazei; Agrocybe aegerita; Auricularia auricular—judae; Calyptella* species; *Coprinus comatus; Cordyceps sinensis; Flammulina velutipes; Ganoderma lucidum; Grifolia frondosa; Hericium erinaceus; Inonotus obliquus; Kuehneromyces* species; *Lentinus edodes; Monascus purpureus; Neolentinus adhaereus; Panus* species; *Phellinus linteus; Pleuroyus ostreatus; Rhizopus oligosporus; Saccharomyces boulardii; Saccharomyces cerevisiae; Schizophyllum commune; Trametes versicolor; Tremella aurantia; Tremella fuciformis*; and *Tricholoma mongolicum*.

9. The composition of claim 6 wherein the fungal species is selected from the group consisting of the following species: *Hericium erinaceus; Ganoderma lucidum; Trametes versicolor; Lentinus edodes; Agaricus bisporus; Agaricus blazei; Flammulina velutipes; Grifola frondosa*; and *Pleuroyus ostreatus*.

10. The composition of claim 6 wherein the edible cell-based growth medium is selected from the group consisting of grains, legumes, tubers, starchy roots, fruits.

11. The composition of claim 6 wherein the edible cell-based growth medium is a grain selected from the group consisting of rye, wheat, corn, rice, oats, millet, barley and triticale.

12. The composition of claim 6 wherein the cells been ruptured by a mixer blade.

13. The composition of claim 12 wherein the extraction medium comprises water and further comprises an edible oil.

14. The composition of claim 12 wherein the extraction medium has been filtered to remove particles that are larger than 40 microns.

15. The composition of claim 12 wherein the composition is free of added denaturing compounds.

16. The composition of claim 12 wherein contents of the ruptured cells have been subjected to a high-pressure treatment following the rupturing.

17. A method of treating a subject, comprising pharmaceutical composition to treat a neurological disorder or cancer, and wherein the pharmaceutical composition is made by a process for preparing high-potency fungal medicinal materials, wherein the process comprises the steps of:
   a) growing organisms from a medicinal fungal species in a culture on a cell-based growth medium, wherein:
      i) the fungal species is a species that is edible when raw; and
      ii) the cell-based growth medium is edible;
   b) placing at least a portion from-the fungal organisms and at least a portion from the cell-based growth medium into an extraction medium, thereby forming a biomass processing medium, wherein the extraction medium is edible and or potable; and
   c) in the biomass processing medium, rupturing substantially all cells of the fungal organisms and the growth medium cells that had been placed therein, thereby forming a medicinal composition, wherein;
      i) the medicinal composition comprises each of the following: contents from the ruptured fungal organisms, contents from the medicinal composition, and the extraction medium; and
      ii) the medicinal composition is edible and or potable; and
   enzymes and other proteins from the fungal organisms of step (a) remain largely undenatured throughout each of steps (a), (b), and (c).

18. The method of claim 17 wherein the fungal species is selected from the group consisting of the following species: *Agaricus bisporus; Agaricus blazei; Agrocybe aegerita; Auricularia auricular—judae; Calyptella* species; *Coprinus comatus; Cordyceps sinensis; Flammulina velutipes; Ganoderma lucidum; Grifolia frondosa; Hericium erinaceus; Inonotus obliquus; Kuehneromyces* species; *Lentinus edodes; Monascus purpureus; Neolentinus adhaereus; Panus* species; *Phellinus linteus; Pleuroyus ostreatus; Rhizopus oligosporus; Saccharomyces boulardii; Saccharomyces cerevisiae; Schizophyllum commune; Trametes versicolor; Tremella aurantia; Tremella fuciformis*; and *Tricholoma mongolicum*.

19. The method of claim 17 wherein the subject has an affliction that is selected from the group consisting of metastatic cancers.

20. The method of claim 19 wherein the affliction is selected from the group consisting of: Parkinson's Disease, Fahr's Disease, Multiple Sclerosis, and depression.

* * * * *